United States Patent [19]

Wangnick et al.

[11] Patent Number: 5,760,229
[45] Date of Patent: Jun. 2, 1998

[54] CRYSTAL MODIFICATION OF 2,4-DIAMINO-6-HYDROXYMETHYLPTERIDINE HYDROBROMIDE

[75] Inventors: Carsten Wangnick, Waldkirch; Peter Merrath, Memmingen, both of Germany

[73] Assignee: Heinric Mack Nachf. Illertissen, Germany

[21] Appl. No.: 597,906

[22] Filed: Feb. 7, 1996

[30] Foreign Application Priority Data

Feb. 7, 1995 [DE] Germany ............ 195 03 966.1

[51] Int. Cl.$^6$ .................................. C02D 428/08
[52] U.S. Cl. .................................... 544/260
[58] Field of Search .......................... 544/260

[56] References Cited

U.S. PATENT DOCUMENTS

| | | | |
|---|---|---|---|
| 4,077,957 | 3/1978 | Piper et al. | 544/260 |
| 4,079,056 | 3/1978 | Piper et al. | 544/260 |
| 4,080,325 | 3/1978 | Ellard | 544/260 |
| 4,306,064 | 12/1981 | Ellard | 544/260 |
| 4,421,913 | 12/1983 | Ellard | 544/260 |
| 4,628,090 | 12/1986 | Coward | 544/260 |
| 5,374,720 | 12/1994 | deGrauss | 544/260 |
| 5,382,582 | 1/1995 | Chan | 544/260 |

*Primary Examiner*—Donald G. Daus
*Attorney, Agent, or Firm*—Felfe & Lynch

[57] ABSTRACT

A novel crystal modification of the compound 2,4-diamino-6-hydroxymethylpteridine hydrobromide and a process for its preparation and its use for preparing methotrexate. The novel crystal modification of 2,4-diamino-6-hydroxymethylpteridine hydrobromide is distinguished in particular by the fact that only one equivalent of the brominating agent triphenylphosphine dibromide is needed for brominating the 6-hydroxymethyl group. No reaction with the amino groups in the 2 and 4 positions takes place. This facilitates the reaction to give 2,4-diamino-6-pteridinyl derivatives such as methotrexate.

7 Claims, No Drawings

CRYSTAL MODIFICATION OF 2,4-DIAMINO-6-HYDROXYMETHYLPTERIDINE HYDROBROMIDE

The present invention relates to a novel crystal modification of the compound 2,4-diamino-6-hydroxymethylpteridine hydrobromide and to a process for its preparation and to its use for preparing methotrexate.

2,4-Diamino-6-hydroxymethylpteridine hydrobromide (DHP-HBr) is an important starting material for the synthesis of N-[4-[((2,4-diamino-6-pteridinyl)methyl)methylaminol]-benzoyl]-L-glutamic acid (methotrexate), which is a folic acid antagonist which has been used for many years as a cytostatic in clinical cancer therapy, for example for leukemia.

Various synthetic routes are known for methotrexate. Its synthesis starting from DHP-HBr is described in U.S. Pat. Nos. 4,079,056 and 4,077,957. First tetraaminopyrimidine and dihydroxyacetone are subjected to a ring closure reaction to give DHP, which is then converted into the hydrobromide. This DHP-HBr is treated with a four-fold excess of triphenylphosphine dibromide. This brominates not only the 6-hydroxymethyl group but also converts the two amino groups in the 2 and 4 positions into phosphazene groups. These groups then have to be hydrolyzed by acidification before reaction with diethyl N-[4-(N-methylamino)benzoyl] glutamate and hydrolysis of the resulting ester gives the desired methotrexate in a yield of about 30%, relative to the DHP-HBr used. The synthetic route described may be illustrated by the following reaction scheme:

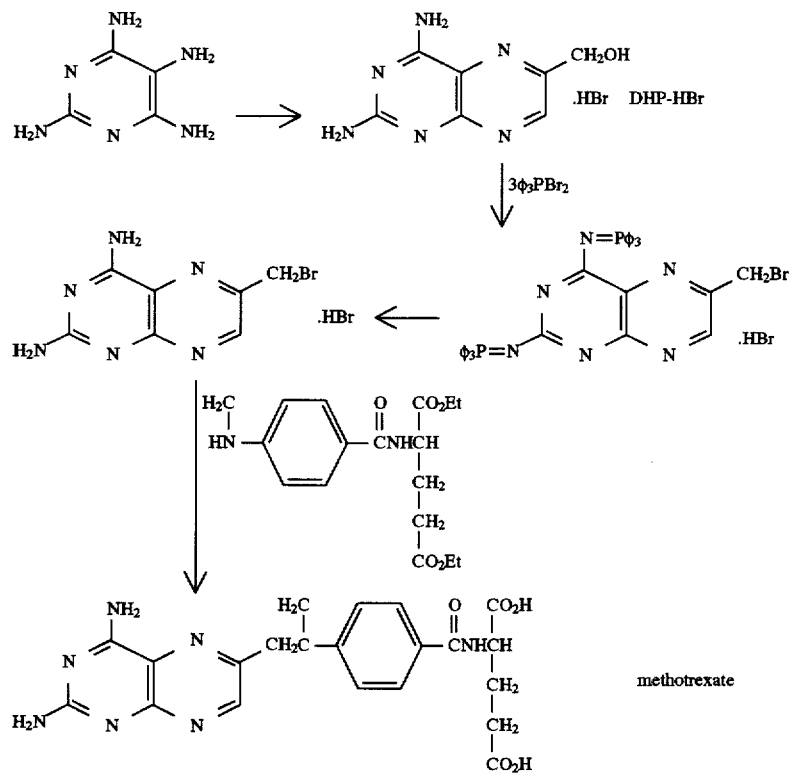

An improved process for synthesizing methotrexate is disclosed in U.S. Pat. No. 4,080,325. Here the DHP is obtained in higher yield and purity by maintaining specific reaction conditions. However, subsequent bromination to give the 2,4-bis(triphenylphosphazeno)-6-bromomethylpteridine is likewise carried out with an at least three-fold excess of triphenylphosphine dibromide. Here the phosphazene groups were not hydrolyzed until after synthesis of the methotrexate/phosphazene derivative.

The object of the present invention is to simplify the synthesis of methotrexate in such a manner that fewer reaction steps are necessary and that methotrexate can be isolated in higher yield and higher degree of purity.

THE INVENTION

It has now been found that DHP-HBr can occur in at least three different crystal modifications. Depending on the crystallization conditions, these modifications can be prepared selectively and distinguished by their X-ray powder diffraction spectra. Surprisingly, it has been found that one of these modifications only reacts with triphenylphosphine dibromide in a molar ratio of 1:1 to give 6-bromomethyl-2,4-diaminopteridine hydrobromide while the amino groups in the 2 and 4 positions do not react to give triphenylphosphazene. This makes it possible to omit the additional process step of hydrolysis of these groups necessary in the prior art. Moreover bromination is virtually quantitative so that it can be followed directly, without isolation or further purification of the 6-bromomethyl-2,4-diaminopteridine hydrobromide, by reaction with diethyl N-[4-(N-methylamino)benzoyl] glutamate in a one-pot procedure to give the diethyl methotrexate and then the desired methotrexate. This significantly increases the yield, while the methotrexate is obtained in very pure form.

Accordingly, the present invention relates to a crystal modification of the compound 2,4-diamino-6-hydroxymethylpteridine hydrobromide (DHP-HBr) whose X-ray powder diffraction spectrum obtained with Cu $K_\alpha$ radiation contains the following high-intensity peaks:

| Angle [°] | $I/I_{max}$ [%] |
|---|---|
| 12.4 | 100 |
| 18.8 | 13 |
| 23.8 | 6 |
| 24.4 | 21 |
| 25.7 | 8 |
| 26.1 | 60 |
| 26.9 | 6 |
| 29.5 | 6 |
| 32.2 | 26 |
| 32.4 | 14 |
| 34.6 | 10 |
| 44.9 | 7 |

The invention also provides a process for preparing the novel crystal modification of DHP-HBr and to the use of this crystal modification of DHP-HBr in the synthesis of methotrexate.

When DHP-HBr is crystallized by customary methods from an HBr-containing ethanolic solution with cooling, orange, rod-like crystals are obtained whose X-ray powder diffraction spectrum obtained with Cu $K_\alpha$ radiation contains the following high-intensity peaks:

| Angle [°] | $I/I_{max}$ [%] |
|---|---|
| 18.5 | 30 |
| 20.6 | 100 |
| 25.6 | 17 |
| 25.8 | 26 |
| 27.9 | 75 |
| 28.5 | 16 |
| 33.3 | 79 |
| 37.4 | 19 |
| 37.7 | 12 |
| 38.5 | 22 |
| 46.6 | 28 |

In contrast, the DHP-HBr crystal modification according to the invention is obtained in the form of beige, leaflet-like crystals. It is formed by crystallizing DHP-HBr from an aqueous HBr-containing solution. The DHP-HBr concentration at the beginning of crystallization should be between 2 and 15% by weight. The pH should have been adjusted to a value below 2, and crystallization should be carried out in the heat at a temperature above 40° C. In order to cause DHP-HBr to crystallize from such a solution, its solubility product must be lowered by addition of bromide ions. Not only hydrobromic acid but also water-soluble salts of hydrobromic acid are suitable for this purpose. Preferably, salts of alkali metals and alkaline earth metals and of ammonia are used. It is also possible to use combinations of various salts and/or hydrobromic acid. Sodium bromide is particularly suitable.

The starting material for the process according to the invention can be either DHP or DHP-HBr. If it is desired to prepare the crystallization solution from DHP, an adequate amount of hydrobromic acid must be added. Acidification of the solution to a pH of <2 and preferably a pH of between 1.5 and 1.9 is also preferably carried out with hydrobromic acid.

Furthermore, for the crystallization of the DHP-HBr modification according to the invention an initial DHP-HBr concentration in water of 5–10% by weight is preferred. The temperature should not exceed 90° C., preference being given in particular to a crystallization temperature of 60°–70° C. The amount of the hydrobromic acid or the salt of hydrobromic acid added is uncritical over a wide range. However, the amount must be sufficient for effecting crystal formation. The concentration of free bromide ions in the crystallization solution should be between 2 and 30% by weight, a concentration of 5–15% by weight being preferred. It is particularly advantageous to inoculate the solution with a crystal of the desired modification.

The DHP-HBr crystal modification thus obtained is particularly suitable for synthesizing methotrexate or other 2,4-diamino-6-pteridinyl compounds since it reacts directly with triphenylphosphine dibromide to give 6-bromomethyl-2,4-diaminopteridine hydrobromide. This is not accompanied by reaction with the amino groups in the 2 and 4 positions, as a result of which in theory a DHP-HBr/triphenylphosphine dibromide molar ratio of 1:1 is sufficient for complete bromination of the 6-hydroxymethyl group.

Accordingly, the invention also relates to the use of the novel DHP-HBr crystal modification in a process for preparing methotrexate, which process comprises a) reacting DHP-HBr having the crystal modification according to the invention with triphenylphosphine dibromide to give 6-bromomethyl-2,4-diaminopteridine hydrobromide, b) reacting this 6-bromomethyl-2,4-diaminopteridine hydrobromide with diethyl N-[4-(N-methylamino)-benzoyl] glutamate to give diethyl methotrexate, and c) liberating the methotrexate by hydrolysis of the diethyl methotrexate.

Preferably a slight excess of triphenylphosphine dibromide of up to about 30%, ie. a DHP-HBr/triphenylphosphine dibromide molar ratio of up to 1:1.3 is used since a portion of the triphenylphosphine dibromide is cleaved hydrolytically by traces of water present in the DHP-HBr or in the solvent.

The bromination can be carried out in any inert solvent and goes to 100% completion as checked by TLC, a value which is markedly higher than that of the prior art. Preferably, the solvent used is dimethylacetamide, in which case the 6-bromomethyl-2,4-diaminopteridine hydrobromide formed precipitates from the reaction solution and can, if desired, be isolated in a yield of about 85% by a simple filtration.

However, an advantageous method is to react the 6-bromo-methyl-2,4-diaminopteridine hydrobromide formed further without any intermediate isolation step to give directly 2,4-diamino-6-pteridinyl derivatives, in particular methotrexate.

According to the invention, DHP-HBr having the novel crystal modification can, for example, be reacted in a one-pot procedure in dimethylacetamide with triphenylphosphine dibromide in a molar ratio of 1:1.0 to 1:1.3 to give 6-bromomethyl-2,4-diaminopteridine hydrobromide.

This intermediate is then reacted directly, without isolating it, with diethyl N-[4-(N-methylamino)benzoyl]-glutamate to give diethyl methotrexate. This reaction too goes virtually to completion.

To isolate and liberate the desired methotrexate, the diethyl ester is then hydrolyzed in a known manner, for example with dilute sodium hydroxide solution. This gives methotrexate in an isolated yield of 75–80% of theory, relative to the DHP-HBr used. Analysis by HPLC indicates a purity of more than 99%.

Using the DHP-HBr crystal modification according to the invention for preparing methotrexate is in particular distinguished by the fact that only one mole of triphenylphosphine dibromide is needed for brominating one mole of DHP-HBr. As compared with the prior art, the amount needed is decreased by a factor of 3–4. This leads to a significant saving in costs but also to a substantial reduction of the amount of triphenylphosphine oxide formed as a waste product. Moreover the reaction of DHP-HBr in the crystal modification according to the invention with triphenylphosphine dibromide is virtually quantitative. This results in a higher yield and higher purity during the further reaction to give methotrexate as compared with the processes disclosed in the prior art.

The examples which follow are intended to illustrate the present invention in more detail:

EXAMPLE 1

Preparation of DHP-HBr in the crystal modification according to the invention 180 g of moist DHP-HBr (dry weight 141 g) (for synthesis, see U.S. Pat. No. 4,080,325) are suspended in 1.6 l of water at 70° C. The pH of the suspension is 2.7–2.8. The pH is brought to 1.5 to 1.6 by addition of 7 ml of 48% hydrobromic acid. This converts the cloudy suspension into a solution. 14 g of activated carbon is added, and the resulting mixture is filtered while maintaining the temperature at 70° C. This is followed by addition of 140 g of sodium bromide and seed crystals (leaflet form) with stirring, giving rise to spontaneous crystallization.

Yield: 111 g of DHP-HBr (leaflet form) HPLC purity>99%.

EXAMPLE 2

Preparation of Methotrexate

A. Preparation of 6-bromomethyl-2,4-diamino pteridine hydrobromide

In a 6-l three-necked flask equipped with stirrer, dropping funnel and thermometer, 475 g of triphenylphosphine is dissolved in 3.75 l of dimethylacetamide (water content as determined by Karl Fischer titration <0.1%), and the resulting solution is cooled to −15° C. to −20° C. 272 g of bromine (1.7 mol) is then added dropwise through the dropping funnel at a uniform rate and with further cooling and vigorous stirring in such a manner that the temperature can be maintained at −10° C. to −15° C. When about 18 ml of bromine has been added, triphenylphosphine dibromide starts precipitating as a colorless solid. The duration of dropwise addition is about 2 hours.

At −10° C., 350 g of DHP-HBr (1.28 mol, leaflet form, water content<1%, prepared by Example 1) is added all at once. The mixture is stirred at −10° C. for 30 minutes, and the temperature is then allowed to rise to 0° C. over a period of 90 minutes. The mixture is stirred at 0° C. for 30 minutes, allowed to warm to 5° C. and stirred at this temperature for another 30 minutes. During this time, the DHP-HBr goes into solution, and the 6-bromomethyl-2,4-diaminopteridine hydrobromide then precipitates very rapidly. The precipitate formed is filtered off with suction and dried.

Yield: 368 g (85% of theory) of 6-bromomethyl-2,4-diaminopteridine hydrobromide

B. Preparation of diethyl methotrexate

6-Bromomethyl-2,4-diaminopteridine hydrobromide is prepared as in Example 2 but not isolated from the reaction solution. The bromination is checked for completion by means of a TLC sample. After reaction is complete, the mixture is warmed to 15° C., and 560 g of diethyl N-[4-(N-methylamino)benzoyl] glutamate are added. The mixture is heated at 50°–55° C. for 7 hours, which after 3–4 hours results in a clear red/orange solution. After 7 hours, the reaction is checked for completion by means of a TLC sample. After reaction is complete, the mixture is cooled to 20° C., and 9.5 l of water at 15° C. are added with stirring. This results in warming to 20°–25° C. At this temperature, 550 ml of 20% sodium hydroxide solution are added dropwise until reaching a pH of 3.8–4.0. During this addition, not only triphenylphosphine oxide but also diethyl methotrexate precipitates. After cooling to 5°–10° C., the precipitate formed is filtered off with suction and washed with 2 l of cold water.

Yield: about 1.8 kg of a moist diethyl methotrexate/triphenylphosphine oxide mixture C. Methotrexate, disodium salt A 20-l glass cylinder equipped with stirrer, dropping funnel and thermometer is charged with 6 l of ethanol. About 1.8 kg of moist diethyl methotrexate/triphenylphosphine oxide mixture (Example 3) is introduced with stirring. The mixture is stirred for 30 minutes, and 2.5 l of water are then added. Stirring is continued for another 15 minutes, the mixture is cooled to 18° C. and a solution of 340 g of 50% sodium hydroxide solution diluted to 1 l with water is added dropwise over a period of about 10 minutes. The temperature is maintained at 20±2° C. by slight cooling. After about 15 minutes, the disodium salt of methotrexate starts precipitating. In order to obtain more readily filterable crystals, another 3 l of ethanol are added over a period of 10 minutes. 45 minutes after the addition of sodium hydroxide solution, the pH is brought to 9.5±0.3 by dropwise addition of about 70 ml of glacial acetic acid. The mixture is cooled to 0°–5° C., maintained at this temperature for 5 hours, and the product is then filtered off with suction. It is washed in portions with a total of 1.5 l of ethanol. The mother liquor contains the entire triphenylphosphine oxide.

Yield: about 1 kg of methotrexate, disodium salt (moist) HPLC purity>99%.

Extrapolation of the weight obtained by drying a small sample gave 586 g of methotrexate, disodium salt (water content by Karl Fischer titration 12.15%), ie. 515 g of anhydrous methotrexate, disodium salt. This corresponds to a theoretical yield of 80.6%, relative to the DHP-HBr used.

D. Methotrexate

The free methotrexate can be obtained from the methotrexate, disodium salt in almost quantitative yield by dissolution in water and acidification to a pH of 4.0.

It will be understood that the specification and examples are illustrative but not limitative of the present invention and that other embodiments within the spirit and scope of the invention will suggest themselves to those skilled in the art.

We claim:

1. A crystal modification of the compound 2,4-diamino-6-hydroxymethylpteridine hydrobromide, wherein the x-ray powder diffraction spectrum of the compound obtained with Cu $K_\alpha$ radiation contains the following high-intensity peaks:

| Angle [°] | $I/I_{max}$ [%] |
| --- | --- |
| 12.4 | 100 |
| 18.8 | 13 |
| 23.8 | 6 |
| 24.4 | 21 |
| 25.7 | 8 |
| 26.1 | 60 |
| 26.9 | 6 |
| 29.5 | 6 |
| 32.2 | 26 |
| 32.4 | 14 |
| 34.6 | 10 |
| 44.9 | 7. |

2. A process for preparing the crystal modification of 2,4-diamino-6-hydroxymethylpteridine hydrobromide (DHP-HBr) of claim 1, consisting essentially of adding HBr or a salt of HBr, to an aqueous solution which consists essentially of water and from 2 to 15 weight percent DHP-HBr and HBr, said aqueous solution having a pH of less than 2, at a temperature above 40° C. so as to form said crystal modification.

3. The process of claim 2, wherein said aqueous solution of DHP-HBr has been prepared by adding HBr to an aqueous solution of DHP.

4. The process of claim 2, wherein said solution contains from 5% to 10% by weight of DHP-HBr.

5. The process of claim 2, wherein said aqueous solution has a pH of from 1.5 to 1.9.

6. The process of claim 2, wherein said temperature is from 60° C. to 70° C.

7. The process of claim 2, wherein said salt of HBr is an alkali metal bromide, an alkaline metal bromide, or an ammonium bromide.

* * * * *